United States Patent [19]

Miyachi et al.

[11] Patent Number: 5,439,919

[45] Date of Patent: Aug. 8, 1995

[54] ARYLGLYCINAMIDE DERIVATIVES AND PREPARATIVE PROCESSES THEREFOR

[75] Inventors: Hiroyuki Miyachi, Kazo; Mitsuru Segawa, Omiya; Emiko Tagami, Otone; Hideo Okubo, Nogi, all of Japan

[73] Assignee: Kyorin Pharmaceutical Co., Ltd., Tokyo, Japan

[21] Appl. No.: 93,854

[22] Filed: Jul. 20, 1993

[30] Foreign Application Priority Data

Jul. 27, 1992 [JP] Japan .................. 4-219699
Jul. 14, 1993 [JP] Japan .................. 5-196882

[51] Int. Cl.⁶ .................. C07C 233/00; C07D 211/30; A01N 43/40
[52] U.S. Cl. .................. 514/316; 514/319; 514/325; 514/330; 514/331; 514/620; 514/423; 514/428; 546/189; 546/195; 546/203; 546/205; 546/220; 546/233; 546/234; 564/164; 564/165; 564/168
[58] Field of Search .................. 546/225, 195, 189, 203, 546/205, 226, 233, 234; 564/164, 165, 168; 514/330, 316, 319, 331, 325, 620, 423, 428; 548/540

[56] References Cited

U.S. PATENT DOCUMENTS 5,153,226 10/1992 Chucholowski et al. .......... 514/617

FOREIGN PATENT DOCUMENTS 0222099 5/1987 European Pat. Off. .
1269556 7/1961 France .

OTHER PUBLICATIONS

Chemical Abstracts, vol. 58, No. 8, Apr. 15, 1963, AN-7913a, S. Kawahara "Alpha-(N-Substituted Animoalkyl) Amino-Alpha-Phenylacetamide".
Chemical Abstracts, vol. 58, No. 8, Apr. 15, 1963, AN-7935d, J. Klosa, "Synthesis of Spasmolytically Active Substances. XVI. Synthesis of Alpha--Phenyl-Alpha-(N,N-Dialkylamnoinoalkyl) Acetamides".

*Primary Examiner*—C. Warren Ivy
*Assistant Examiner*—Raymond Covington
*Attorney, Agent, or Firm*—Oblon, Spivak, McClelland, Maier, & Neustadt

[57] ABSTRACT

Arylglycinamide derivatives represented by a general formula (1)

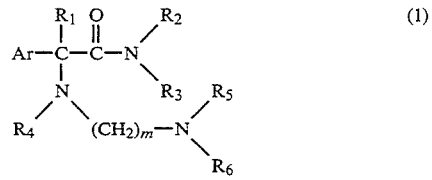

(wherein Ar denotes a phenyl group which may have 1 to 3 substituents or naphthyl group which may have 1 to 3 substituents, $R_1$ and $R_4$ denote identically or differently hydrogen atoms or lower alkyl groups with 1 to 3 carbon atoms, $R_2$ denotes a lower alkyl group with 1 to 6 carbon atoms, cycloalkyl group with 3 to 6 carbon atoms, lower alkyl group with 1 to 4 carbon atoms which may have a phenyl group which may have 1 to 3 substituents, norbornyl group, adamantyl group or phenyl group which may have 1 to 3 substituents, $R_3$ denotes a hydrogen atom or lower alkyl group with 1 to 6 carbon atoms or it may form a ring constituting alkylene together with $R_2$, $R_5$ denotes a lower alkyl group with 1 to 6 carbon atoms or cycloalkyl group with 5 or 6 carbon atoms, $R_6$ denotes a hydrogen atom or lower alkyl group with 1 to 6 carbon atoms or it may form a ring constituting alkylene together with $R_5$, and m denotes 2 or 3), and their salts, which function as effective therapeutic drugs for the dysurias such as urinary incontinence and pollakiuria, and the preparative processes therefor are presented.

2 Claims, No Drawings

ARYLGLYCINAMIDE DERIVATIVES AND PREPARATIVE PROCESSES THEREFOR

BACKGROUND OF THE INVENTION

The present invention relates to novel arylglycinamide derivatives and their salts effective as therapeutic agents for the dysurias such as urinary incontinence and pollakiuria.

Urinary incontinence and pollakiuria give mental pains to the patients predisposing them to social isolation. These neurogenic bladder dysfunctions are characterized by overactive detrusor, in part.

Anticholinergic drugs are used in treatment of urinary bladder dysfunctions associated with overactive detrusor, including oxybutynin hydrochloride and terodiline hydrochloride. Clinically, these drugs are effective for treatment of syndrome elicited by bladder activity, but they frequently cause the adverse effects such as dry mouth and urinary retention. The occurrence of such adverse effects is considered to be caused by non-selective anticholinergic action of these drugs, in part. Hence, new therapeutic drugs for urinary incontinence and pollakiuria that cause no serious adverse effects such as dry mouth, anuresis and difficulty in micturition have been desired strongly.

As for the arylglycinamide derivatives, there are reports on phenylglycine ester (Yakugaku Zasshi, 73, 1327 (1953)) and mandelic ester derivatives (J. Am. Chem. Soc., 70, 4214 (1948)) having an antispasmodic action, but they are different in structure from the novel compounds of the present invention. Moreover, there are no reports on the arylglycinamide derivatives having the therapeutic effect on the dysurias such as urinary incontinence and pollakiuria.

The present invention is for providing drugs that allow the therapy of urinary incontinence and pollakiuria without causing dry mouth, anuresis or difficulty in micturition being the adverse effects of conventional therapeutic drugs for urinary incontinence and pollakiuria.

SUMMARY OF THE INVENTION

The inventors paid an attention to arylglycinamide derivatives for the purpose aforementioned and, as a result of diligent studies, we have found that novel arylglycinamide derivatives represented by a general formula (1)

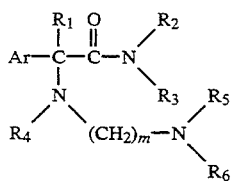

(wherein Ar denotes a phenyl group which may have 1 to 3 substituents or naphthyl group which may have 1 to 3 substituents, $R_1$ and $R_4$ denote identically or differently hydrogen atoms or lower alkyl groups with 1 to 3 carbon atoms, $R_2$ denotes a lower alkyl group with 1 to 6 carbon atoms, cycloalkyl group with 3 to 6 carbon atoms, lower alkyl group with 1 to 4 carbon atoms which may have a phenyl group which may have 1 to 3 substituents, norbornyl group, adamantyl group or phenyl group which may have 1 to 3 substituents, $R_3$ denotes a hydrogen atom or lower alkyl group with 1 to 6 carbon atoms or it may form a ring constituting alkylene together with $R_2$, $R_5$ denotes a lower alkyl group with 1 to 6 carbon atoms or cycloalkyl group with 5 or 6 carbon atoms, $R_6$ denotes a hydrogen atom or lower alkyl group with 1 to 6 carbon atoms or it may form a ring constituting alkylene together with $R_5$, and m denotes 2 or 3), and their salts, without showing the adverse effects of existing drugs, inhibit the overactivity of bladder, and increase the volume of bladder, leading to the completion of the present invention.

DETAILED DESCRIPTION OF THE INVENTION

As the "substituents" of phenyl group or naphthyl group shown in the invention, halogen, lower alkyl group, lower alkoxy group, phenyl group, hydroxyl group, etc. can be mentioned. As the "halogens", fluorine, chlorine and bromine are mentioned. As the "lower alkyl groups", straight chain or branched ones with 1 to 6 carbon atoms such as methyl, ethyl, n-propyl, i-propyl, n-butyl and t-butyl are mentioned. As the "lower alkoxy groups", ones with 1 to 3 carbon atoms such as methoxy, ethoxy and n-propoxy are mentioned. As the "cycloalkyl groups", alicyclic hydrocarbons with 3 to 6 carbon atoms such as cyclopentyl and cyclohexyl, and the like are mentioned. As the "alkylenes", ones with 3 to 6 carbon atoms such as tetramethylene and pentamethylene are mentioned.

In the invention, compounds represented by the general formula (1)

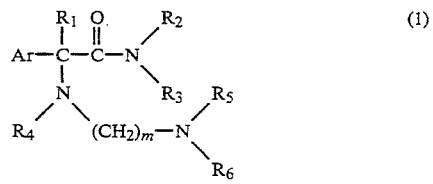

(wherein Ar, $R_1$, $R_2$, $R_3$, $R_4$, $R_5$, $R_6$ and m are same as above), can be prepared by reacting compounds represented by a general formula (3)

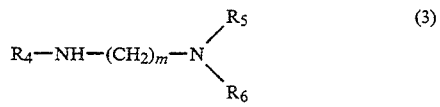

(wherein $R_4$, $R_5$, $R_6$ and m are same as above), with compounds represented by a general formula (2)

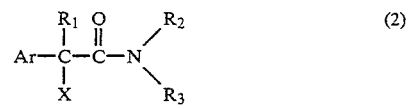

(wherein Ar, $R_1$, $R_2$ and $R_3$ are same as above, and X denotes an eliminating group), preferably in the presence of base. Here, as the "eliminating groups", halogen, aliphatic sulfonyloxy group such as mesyloxy group, aromatic sulfonyloxy group such as tosyloxy group, and the like can be mentioned.

It is desirable to conduct the reaction at 0° to 150° C. in an organic solvent such as dimethylformamide, dimethyl sulfoxide, dichloromethane, chloroform, benzene, toluene or xylene in the presence of inorganic base including alkali metal hydroxide such as sodium hydroxide or potassium hydroxide, alkali metal carbonate such as sodium carbonate or potassium carbonate, alkali metal bicarbonate such as sodium hydrogen carbonate or potassium hydrogen carbonate, alkaline earth metal hydroxide such as magnesium hydroxide or calcium hydroxide, metal hydride such as sodium hydride, or the like, or organic base including tertiary amine such as pyridine, or the like as a base.

Moreover, in the invention, compounds represented by a general formula (4)

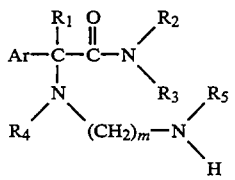

(wherein Ar, $R_1$, $R_2$, $R_3$, $R_4$, $R_5$ and m are same as above), can be prepared by subjecting compounds represented by a general formula ( 6 )

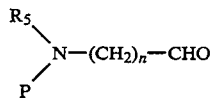

(wherein $R_5$ is same as above, P denotes a protecting group, and n denotes 1 or 2), to the reductive amination with compounds represented by a general formula (5)

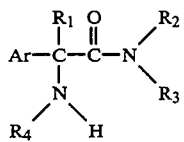

(wherein Ar, $R_1$, $R_2$, $R_3$ and $R_4$ are same as above), and then deprotecting the protective group of compounds (7) obtained

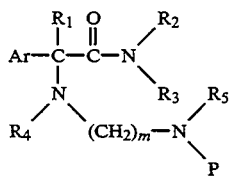

(wherein Ar, $R_1$, $R_2$, $R_3$, $R_4$, $R_5$, m and P are same as above).

Here, as the protective groups, carbamate groups such as ethoxy carbonyl and tert-butoxy carbonyl can be mentioned.

It is desirable to conduct the reductive amination at 0° to 100 ° C. in an organic solvent such as methanol, ethanol, benzene and dimethylformamide using noble metal catalyst such as palladium on carbon or platinum oxide, sodium borohydride, sodium cyanoborohydride, or the like as a reducing agent. The deprotecting reaction is desirable to conduct at 0° to 100 ° C. under acidic condition with trifluoroacetic acid, hydrochloric acid, hydrobromic acid or the like.

Besides, since the arylglycinamide derivatives of the invention have an asymmetric carbon atom adjacent to carbonyl group, at least 2 or more kinds of optical isomers exist, but these isomers and mixtures are all included in the invention.

The preparation of optical isomers can be achieved by fractionatingly recrystallizing a salt with optically active acid such as, for example, 10-camphorsulfonic acid, tartaric acid or O,O-dibenzoyltartaric acid from suitable solvent. Also, they can be prepared by stereoselective synthetic method. Further, they can be prepared by chromatographic technology using chiral stationary phase.

Moreover, the novel compounds of the invention can be converted to acid adducts by reacting with physiologically usable inorganic acids, for example, hydrochloric acid, sulfuric acid, hydrobromic acid and phosphoric acid, or organic acids, for example, maleic acid, fumaric acid, tartaric acid, oxalic acid, D-camphorsulfonic acid, D-(+)-dibenzoyltartaric acid, etc. according to usual method.

Furthermore, as the administration forms of the novel compounds of the invention, oral administration with, for example, tablets, capsules, granules, powders, sirups or the like, or parenteral administration with injections, suppositories or the like can be mentioned.

In following, the invention will be illustrated in detail based on the examples.

REFERENTIAL EXAMPLE 1

N-cyclohexyl-α-bromophenylacetamide

To a mixture of cyclohexylamine (10.9 g), triethylemine (11.1 g) and chloroform (200 ml), α-bromophenylacetyl chloride (23.3 g) was added dropwise over 10 minutes under cooling with ice and stirring, and the mixture was refluxed for 10 hours. After cooling by allowing to stand, the reaction mixture was washed with 0.5N hydrochloric acid (100 ml), with 0.5N aqueous solution of sodium hydroxide (100 ml) and with saturated saline solution (100 ml), and then concentrated. The residue was recrystallized from ethyl acetate-ethanol to obtain 12.2 g of title compound as colorless crystals. The mother liquor from recrystallization was concentrated and the residue was purified by means of column chromatography (developing solvent, chloroform:ethanol=20 : 1) to obtain 13.0 g of additional title compound as colorless crystals (overall yield 85.4%).

Melting point: 126°–127 ° C.

H-NMR (CDCl$_3$) δ: 7.30–7.44 (5H, m), 6.56 (1H, brs), 5.42 (1H, s), 3.77–3.84 (1H, m), 1.94 (2H, brs), 1.72–1.74 (2H, brs), 1.57–1.64 (1H, m), 1.35–1.44 (3H, m), 1.20–1.29 (5H, m).

Example 1

N-cyclohexyl-α-[[2-(tert-butylamino)ethyl]amino]-phenylacetamide

A mixture of N-cyclohexyl-α-bromophenylacetamide (2.37 g), N-tert-butylethylenediamine (2.00 g), triethylamine (1.12 ml) and toluene (30 ml) was refluxed for 18 hours. The reaction mixture was concentrated and the residue was purified by means of alumina column chromatography (developing solvent, ethyl acetate) and then distilled under reduced pressure to obtain 1.03 g (38.9%) of title compound as a colorless oily product.

Boiling point: 200 ° C. (2.0 mmHg)

Elemental analysis (%): As $C_{20}H_{33}N_3O$ Calculated C: 72.46 H: 10.03 N: 12.68 Observed C: 72.33 H: 10.19 N: 12.61

Mass spectrum (m/z): 331 (M³⁰), 245, 205, 149
H-NMR (CDCl₃): 7.27–7.38 (5H, m), 7.12 (1H, s), 4.12 (1H, s), 3.76–3.78 (1H, m), 2.65–2.69 (4H, m), 1.88 (3H, m), 1.58–1.68 (3H, m), 1.34–1.40 (2){, m), 1.16–1.23 (2H, m), 1.08 (9H, s)

Example 2

N, N-diethyl-α- [[2-( tert-butylamino )ethyl]amino]phenylacetamide

Similarly to Example 1, 1.60 g (26.2%) of title compound were obtained as a yellow oily product.
Boiling point: 190 °C. (0.5 mmHg)
Elemental analysis (%): As C₁₈H₃₁N₃O.1/9H₂O Calculated C: 70.32 H: 10.23 N: 13.67 Observed C: 70.23 H: 10.30 N: 13.50.
Mass spectrum (m/z): 305 (M³⁰), 290, 219
H-NMR (CDCl₃) δ: 7.27–7.33 (5H, m), 4.44 (1H, s), 3.50–3.55 (1H, m), 3.24–3.33 (2H, m), 3.06 3.12 (1H, m), 2.52–2.73 (4){, m), 1.09–1.12 (3H, t, J 7.3 Hz), 1.08 (9H, s), 0.98–1.02 (3H, t, J =7.3 Hz)

Example 3

N-tert-butyl-α- [[2- (diethylamino )ethyl]amino]phenylacetamide

Similarly to Example 1, 10.00 g (65.5%) of title compound were obtained as colorless crystals.
Melting point: 50°–52 °C. (n-hexane)
Elemental analysis (%): As C₁₈H₃₁N₃O.1/10H₂O Calculated C: 70.78 H: 10.23 N: 13.76 Observed C: 70.44 H: 10.31 N: 13.74.
Mass spectrum (m/z): 305 (M³⁰), 205, 163
H-NMR (CDCl₃) δ: 7.26–7.34 (5H, m), 4.01 (1H, s), 2.63–2.65 (2H, m), 2.47–2.56 (6H, m), 1.35 (9H, s), 0.96–1.00 (6H, t, J =7.3 Hz)

Example 4 through 45

According to the process of Example 1, compounds represented by the following general formula (1) were synthesized as shown in Table 1 through Table 8.

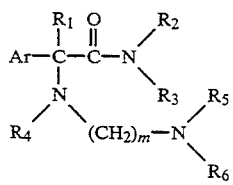

(1)

TABLE 1

| Example | Ar | R₁ | R₂ | R₃ | R₄ |
|---|---|---|---|---|---|
| 4 | phenyl | H | CH₃CH₂— | CH₃CH₂— | H |
| 5 | phenyl | H | CH₃CH₂— | CH₃CH₂— | H |
| 6 | phenyl | H | CH₃CH₂— | CH₃CH₂— | H |
| 7 | phenyl | H | CH₃CH₂— | CH₃CH₂— | H |
| 8 | phenyl | H | CH₃CH₂— | CH₃CH₂— | H |
| 9 | phenyl | H | (CH₃)₂CH— | H | H |
| 10 | phenyl | H | (CH₃)₂CH— | (CH₃)₂CH— | H |
| 11 | phenyl | H | (CH₃)₂CH— | (CH₃)₂CH— | H |
| 12 | phenyl | H | (CH₃)₃C— | H | H |
| 13 | phenyl | H | (CH₃)₃C— | H | H |
| 14 | phenyl | H | (CH₃)₃C— | H | CH₃— |

TABLE 2

| Example | R₅ | R₈ | m | bp °C. (mmHg) | Mass spectrum m/z |
|---|---|---|---|---|---|
| 4 | (CH₃)₂CH— | H | 2 | 160(0.1) | 291(M⁺) 219, 191 |
| 5 | CH₃— | CH₃— | 2 | 245(0.25) | 277(M⁺) 219, 177 |
| 6 | CH₃CH₂— | CH₃CH₂— | 2 | 240(0.2) | 305(M⁺) 219, 162 |
| 7 | (CH₃)₂CH— | (CH₃)₂CH— | 2 | 250(0.2) | 333(M⁺) 290, 288 |
| 8 | —(CH₂)₅— | | 2 | 220~250(0.25) | 317(M⁺) |

TABLE 2-continued

| Example | R5 | R8 | m | bp °C. (mmHg) | Mass sspectrum m/z |
|---|---|---|---|---|---|
| 9 | CH3— | CH3— | 2 | *1 | 217, 162 263(M+) |
| 10 | CH3CH2— | CH3CH2— | 2 | 150(0.3) | 205, 177 333(M+) |
| 11 | —(CH2)4— | | 2 | 190(0.25) | 318, 247 331(M+) |
| 12 | (CH3)2CH— | H | 2 | 150(0.2) | 247, 203 291(M+) |
| 13 | (CH3)3C— | H | 2 | 190(0.9) | 191, 86 305(M+) |
| 14 | CH3CH2— | CH3CH2— | 2 | 160(0.1) | 205, 127 319(M+) 304, 205 |

*1: mp 89~92° C.

TABLE 3

| Example | Ar | R1 | R2 | R3 | R4 |
|---|---|---|---|---|---|
| 15 |  | H | (CH3)3C— | H | H |
| 16 |  | H | (CH3)3C— | H | H |
| 17 |  | H | (CH3)3C— | CH3— | H |
| 18 |  | H | (CH3)3C— | CH3— | H |
| 19 |  | H | (CH3)3C— | CH3— | H |
| 20 |  | H | (CH3)2CHCH2CH2— | H | H |
| 21 |  | H | (CH3)2CHCH2CH2— | H | H |
| 22 |  | H | (CH3)2CHCH2CH2— | H | H |
| 23 |  | H | (CH3)2CHCH2CH2— | H | H |
| 24 |  | H | (CH3)3CCH2— | H | H |
| 25 |  | H | (CH3)3CCH2— | H | H |

TABLE 4

| Example | R5 | R8 | m | bp °C. (mmHg) | Mass spectrum m/z |
|---|---|---|---|---|---|
| 15 | (CH3)2CH— | (CH3)2CH— | 2 | 165(0.13) | 333(M+) 318, 290 |
| 16 | —(CH2)4— | | 2 | *2 | 303(M+) 219, 203 |
| 17 | CH3CH2— | CH3CH2— | 2 | 160(0.15) | 319(M+) 305, 205 |
| 18 | (CH3)2CH— | (CH3)2CH— | 2 | 180(0.2) | 347(M+) 304, 233 |
| 19 | —(CH2)4— | | 2 | 170(0.1) | 317(M+) 276, 233 |
| 20 | CH3— | CH3— | 2 | 250(0.3) | 291(M+) 233, 177 |
| 21 | CH3— | CH3— | 3 | 250(0.15) | 305(M+) 177, 106 |
| 22 | CH3CH2— | CH3CH2— | 2 | 245(0.5) | 319(M+) 233, 205 |
| 23 | (CH3)2CH— | (CH3)2CH— | 2 | 250(0.4) | 347(M+) 304, 233 |
| 24 | (CH3)2CH— | H | 2 | 150(0.15) | 305(M+) 233, 191 |
| 25 | CH3— | CH3— | 2 | 245(0.2) | 291(M+) |

TABLE 4-continued
| Example | R5 | R8 | m | bp °C. (mmHg) | Mass spectrum m/z |
|---|---|---|---|---|---|
| | | | | | 233, 177 |
*2: mp 79~81° C.
TABLE 5
| Example | Ar | R1 | R2 | R3 | R4 |
|---|---|---|---|---|---|
| 26 |  | H | CH3CH2C(CH3)2— | H | H |
| 27 |  | H | CH3CH2C(CH3)2— | H | H |
| 28 |  | H |  | H | H |
| 29 |  | H |  | H | H |
| 30 |  | H |  | H | H |
| 31 |  | H |  | H | H |
| 32 |  | H |  | H | CH3— |
| 33 |  | H |  | H | H |
| 34 |  | H | 2-Norbornyl | H | H |
| 35 |  | H | 2-Norbornyl | H | H |
| 36 |  | H | 2-Norboryl | H | H |
TABLE 6
| Example | R5 | R8 | m | bp °C. (mmHg) | Mass spectrum m/z |
|---|---|---|---|---|---|
| 26 | (CH3)3C— | H | 2 | 210(0.2) | 319(M+) 233, 219 |
| 27 | CH3CH2— | CH3CH2— | 2 | 160(0.3) | 319(M+) 233, 163 |
| 28 | CH3CH2— | CH3CH2— | 2 | 245(0.8) | 317(M+) 231, 205 |
| 29 | —(CH2)4— | | 2 | 250(0.3) | 315(M+) 231, 203 |
| 30 | CH3— | CH3— | 2 | 200(0.2) | 303(M+) 245, 177 |
| 31 | CH3CH2— | CH3CH2— | 2 | 250(0.3) | 331(M+) 245, 205 |
| 32 | CH3CH2— | CH3CH2— | 2 | *3 | 345(M+) 259, 188 |
| 33 | (CH3)2CH— | (CH3)2CH— | 2 | 210(0.1) | 359(M+) 316, 233 |
| 34 | (CH3)2CH— | H | 2 | 190(0.1) | 329(M+) 257, 191 |
| 35 | (CH3)3C— | H | 2 | 200(0.9) | 343(M+) 328, 257 |
| 36 | (CH3)2CH— | (CH3)2CH— | 2 | 245(0.2) | 371(M+) 328, 233 |
*3: mp 103~105° C.

TABLE 7
| Example | Ar | $R_1$ | $R_2$ | $R_3$ | $R_4$ |
|---|---|---|---|---|---|
| 37 |  | H | 1-Adamantyl | H | H |
| 38 |  | H | 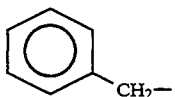 | H | H |
| 39 |  | H | 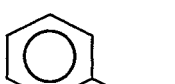 | $CH_3-$ | H |
| 40 |  | H | 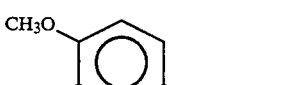 | H | H |
| 41 |  | H | 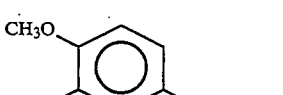 | $CH_3-$ | H |
| 42 |  | H |  | H | H |
| 43 | 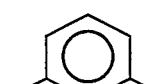 | H | $(CH_3)_3C-$ | H | H |
| 44 | 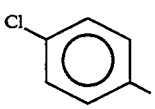 | H | $(CH_3)_3C-$ | H | H |
| 45 | 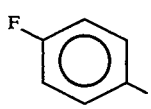 | H | $(CH_3)_3C-$ | H | H |
TABLE 8
| Example | $R_5$ | $R_6$ | m | bp °C. (mmHg) | Mass spectrum m/z |
|---|---|---|---|---|---|
| 37 | $CH_3CH_2-$ | $CH_3CH_2-$ | 2 | *4 | 384($M^+$) 298, 205 |
| 38 | $CH_3CH_2-$ | $CH_3CH_2-$ | 2 | 230(0.2) | 339($M^+$) 253, 205 |
| 39 | $(CH_3)_3C-$ | H | 2 | 190(0.5) | 353($M^+$) 267, 255 |
| 40 | $CH_3CH_2-$ | $CH_3CH_2-$ | 2 | 250(0.2) | 413($M^+$) 327, 164 |
| 41 | $CH_3CH_2-$ | $CH_3CH_2-$ | 2 | 250(0.2) | 427($M^+$) 341, 205 |
| 42 | $CH_3CH_2-$ | $CH_3CH_2-$ | 2 | 200(0.2) | 381($M^+$) 366, 205 |
| 43 | $CH_3CH_2-$ | $CH_3CH_2-$ | 2 | 160(0.6) | 339($M^+$) 239, 86 |
| 44 | $CH_3CH_2-$ | $CH_3CH_2-$ | 2 | 155(0.7) | 339($M^+$) 239, 86 |
| 45 | $CH_3CH_2-$ | $CH_3CH_2-$ | 2 | 150(0.6) | 323($M^+$) 223, 86 |
*4: mp 71~72° C.

Example 46

N-cyclohexyl-a-[[2-(tert-butylamino)ethyl]amino]-phenylacetamide.1 maleate

N-cyclohexyl-α-[[2-(tert-butylamino)ethyl]amino]-phenylacetamide (0.50 g) was dissolved into ethyl acetate (15 ml) and, after anhydrous maleic acid (0.17 g) and ethanol (2 ml) were added and dissolved under heat, the solution was allowed to stand for 2 days in a refrigerator. After the crystals deposited were collected by filtration, they were dried to obtain 0.32 g (47.3%) of title compound.

Melting point: 152°-154 °C.

Elemental analysis (%): As $C_{20}H_{33}N_3O \cdot C_4H_4O_4$ Calculated C: 64.39 H: 8.34 N: 9.39 Observed C: 64.37 H: 8.36 N: 9.38.

Example 47

N,N-diethyl-α-[[2-(tert-butylamino)ethyl]amino]-phenylacetamide.1 maleate

Similarly to Example 46, 0.50 g (72.5%) of title compound were obtained as colorless crystals.

Melting point: 107°-110 °C.

Elemental analysis (%): As $C_{18}H_{31}N_3O \cdot C_4H_4O_4$ Calculated C: 62.69 H: 8.37 N: 9.97 Observed C: 62.57 H: 8.44 N: 9.80.

Example 48

N-tert-butyl-α-[[2 - ( diethylamino ) ethyl]amino]phenylacetamide.1 maleate

Similarly to Example 46, 0.45 g (67.2%) of title compound were obtained as colorless crystals.

Melting point: 89°-91 °C.

Elemental analysis (%): As $C_{18}H_{31}N_3O \cdot C_4H_4O_4$ Calculated C: 62.69 H: 8.37 N: 9.97 Observed C: 62.63 H: 8.48 N: 9.90.

Example 49 through 53

According to the process of Example 46, compounds resented by a following general formula (8) were synthesized as shown in Tables 9 and 10.

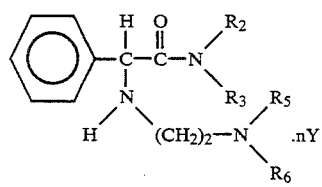 (8)

TABLE 9

| Example | R2 | R3 | R5 | R6 | Y | n |
|---------|----|----|----|----|---|---|
| 49 | (CH3)3C— | H | CH3CH2— | CH3CH2— | Oxalic acid | 1 |
| 50 | (CH3)3C— | H | CH3CH2— | CH3CH2— | D-camphorsulfonic acid | 2 |
| 51 | cyclohexyl | H | (CH3)3C— | H | Oxalic acid | 1 |

TABLE 9-continued

| Example | R2 | R3 | R5 | R6 | Y | n |
|---------|----|----|----|----|---|---|
| 52 | cyclohexyl | H | (CH3)3C— | H | Fumaric acid | 1 |
| 53 | cyclohexyl | H | (CH3)3C— | H | D-(+)-dibenzoyltartaric acid | 1 |

TABLE 10

| Example | mp °C. | Elemental analysis (%) | | | Calc./obs. |
|---------|--------|---|---|---|---|
| 49 | 113~116 | C; 56.11 55.93 | H; 7.62 7.78 | N; 9.35 9.18 | *1 |
| 50 | 214~217 | C; 59.27 58.95 | H; 8.24 8.33 | N; 5.46 5.55 | |
| 51 | 176~178 | C; 61.81 61.99 | H; 8.40 8.34 | N; 9.83 9.79 | *2 |
| 52 | 120~124 | C; 63.56 63.61 | H; 8.36 8.43 | N; 9.27 9.36 | *2 |
| 53 | 135*4 | C; 65.88 65.72 | H; 6.88 7.00 | N; 6.07 6.08 | *3 |

*1 As ½ H2O
*2 As ¼ H2O
*3 As 1/6 H2O
*4 Decomposition point

REFERENTIAL EXAMPLE 2

N-tert-butoxycarbonyl-N-tert-bu-tylglycinal

To N-tert-butoxycarbonyl-N-tert-butylethanolamine (7.24 g), triethylamine (13.5 g) and methylene chloride (150 ml) in 500 ml round bottom flask, a solution dissolved sulfur trioxide-pyridine complex (15.9 g) into 150 ml of DMSO was added at a time under cooling with ice and stirring. After stirring for 10 minutes at room temperature, the reaction mixture was poured into 1 liter of saturated saline solution. After the methylene chloride layer was separated, the aqueous layer was extracted with ether and all of the organic layers were combined, which was dried over anhydrous sodium sulfate and then concentrated. The residue was purified by means of silica gel chromatography (chloroform: ethanol=20:1) to obtain 6.80 g of aimed product as a faintly yellow oily product. Yield: 94.8%

Example 54

(S)-N, N-diethyl-2-(2-tert-butylaminoethylamino)-2-phenylacetamide.1 maleate In a 100 ml reaction bottle for medium pressure catalytic reduction, (S)-2-phenylglycinediethylamide (0.90 g), N-tert-butoxycarbonyl-N-tert-butylglycinal (1.80 g), 10 palladium on carbon (1.06 g), molecular sieves, 4A, activated powder (9.03 g) and ethanol (50.0 ml) were charged, and hydrogenation was conducted for 10 hours at room temperature at an initial pressure of 3.6 kg/cm. The insolubles were filtered and washed with ethanol, and then the filtrate was concentrated. To the residue, 30.0 ml of trifluoroacetic acid was added under cooling with ice. After the mixture was stirred for 1 hour at room temperature, excess trifluoroacetic acid was distilled off under reduced pressure. To the residue, 100 ml of water and 40.0 ml of 28% aqueous ammonia were added, which was extracted with $CHCl_3$. The organic layer was dried over anhydrous sodium sulfate and then concentrated. The residue was purified by means of alumina column chromatography (ethyl acetate) and treated with maleic acid, thereby obtaining 730 mg (yuekd 39.6%) of (S)-N, N-diethyl-2-(2-tert-butylaminoethyl)-2-phenylacetamide.1 maleate as colorless crystalline powders.

Melting point: 111°–113 ° C. (ethyl acetate)
$[\alpha]_D^{20} = +60.88°$ (C=0.722, EtOH)
Elemental analysis ( % ): As $C_{18}H_{31}N_3O \cdot C_4H_4O_4$.
Calculated C: 62.69 H: 8.37 N: 9.97 Observed C: 62.38 H: 8.17 N: 9.92.

NMR (400 MHz, $d_6$ DMSO, δ) 7.34–7.40 (m, 5H), 6.04 (S, H), 4.76 (m, 1H), 3.22–3.37 (m, 4H), 2.95–2.96 (m, 2H), 2.65 (m, 2H), 1.25 (S, 9H), 0.99–1.02 (t, 3H, J =6.8 Hz), 0.84–0.88 (t, 3It, J =6.8 Hz)

The optical purity of the optically active substance obtained was 99.8% e.e. through the analysis with HPLC (column: Chiral cel OD-R) used chiral column.

Example 55 through 66

By the same procedure as Example 54, compounds represented by the following general formula (1) were synthesized as shown in Tables 11 and 12.

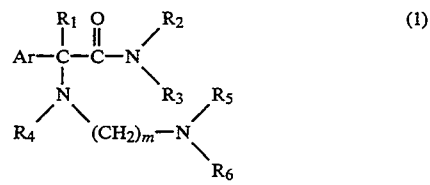

TABLE 11

| Example | Ar | $R_1$ | $R_2$ | $R_3$ | $R_4$ | $R_5$ | $R_6$ | m |
|---|---|---|---|---|---|---|---|---|
| 55 | $CH_3O$-C$_6$H$_4$- | H | $CH_3CH_2$— | $CH_3CH_2$— | H | $(CH_3)_3C$— | H | 2 |
| 56 | $(CH_3)_2CH$-C$_6$H$_4$- | H | $CH_3CH_2$— | $CH_3CH_2$— | H | $(CH_3)_3C$— | H | 2 |
| 57 | naphthyl | H | $CH_3CH_2$— | $CH_3CH_2$— | H | $(CH_3)_3C$— | H | 2 |
| 58 | $CH_3$-C$_6$H$_4$- | H | $CH_3CH_2$— | $CH_3CH_2$— | H | $(CH_3)_3C$— | H | 2 |
| 59 | phenyl | H | 4-$CH_3O$-C$_6$H$_4$- | H | H | $(CH_3)_3C$— | H | 2 |
| 60 | phenyl | H | $CH_3CH_2$— | $CH_3CH_2$— | H | $(CH_3)_2CH$— | H | 2 |
| 61 | phenyl | H | cyclohexyl | H | H | $(CH_3)_2CH$— | H | 2 |
| 62 | phenyl | H | cyclopropyl | H | H | $(CH_3)_3C$— | H | 2 |
| 63 | phenyl | H | —$(CH_2)_5$— | | H | $(CH_3)_3C$— | H | 2 |

TABLE 11-continued

| Example | Ar | R1 | R2 | R3 | R4 | R5 | R6 | m |
|---|---|---|---|---|---|---|---|---|
| 64 | 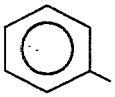 | H |  | H | H | (CH3)3C— | H | 2 |
| 65 | 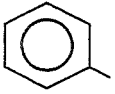 | H | —(CH2)4— | | H | (CH3)3C— | H | 2 |
| 66 | 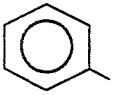 | H | CH3CH2— | CH3CH2— | H | (CH3)3C— | H | 2 |
| 67 | 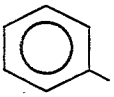 | H |  | H | H | CH3(CH2)3— | H | 2 |

TABLE 12

| Example | Stereo-form at 2-position | Salt | bp °C.(mmHg), [mp °C.] | Mass spectrum m/z | Angle of rotation (°C.) |
|---|---|---|---|---|---|
| 55 | Racemate | — | 230(0.4) | 335(M+) 235, 220 | — |
| 56 | Racemate | — | 210(0.5) | 347(M+) 261, 247 | — |
| 57 | Racemate | — | [88~90] | 355(M+) 269, 255 | — |
| 58 | Racemate | — | 200(0.3) | 319(M+) 233, 219 | — |
| 59 | Racemate | — | 230(0.3) | 355(M+) 269, 240 | — |
| 60 | S form | 1 Maleic acid | [106~108] | 291(M+) 219, 207 | $[\alpha]_D^{20}$ +65.16 (C = 0.646, EtOH) |
| 61 | S form | 1 Maleic acid | [104~106] | 317(M+) 245, 191 | $[\alpha_D^{20}$ +31.46 (C = 0.57, EtOH) |
| 62 | S form | 1 Maleic acid | [151~153] | 289(M+) 274, 205 | $[\alpha]_D^{20}$ +36.75 (C = 0.370, EtOH) |
| 63 | S form | 1.5 Oxalic acid | [184~187] | 317(M+) 231, 219 | $[\alpha]_D^{20}$ +40.87 (C = 0.388, DMSO) |
| 64 | S form | 1 Maleic acid | [142~144] | 317(M+) 302, 231 | $[\alpha]_D^{20}$ +24.49 (C = 0.564, EtOH) |
| 65 | S form | 1 Maleic acid | [155~157] | 303(M+) 217, 205 | $[\alpha]_D^{20}$ +40.52 (C = 0.320, EtOH) |
| 66 | R form | 1 Maleic acid | [111~114] | 305(M+) 290, 205 | $[\alpha]_D^{20}$ −57.91 (C = 0.268, EtOH) |
| 67 | S form | 1.5 Maleic acid | [157-159] | 331(M+) 245, 205 | $[\alpha]_D^{20}$ +33.37 (C = 0.28, EtOH) |

EXPERIMENTAL EXAMPLE 1

Anticholinergic action on the specimen of isolated guinea pig ileum

A specimen (length ca. 2 cm) of male guinea pig ileum was suspended into a 10 ml-organ bath filled up with Tyrode solution. The Tyrode solution was constantly gassed with 95% $O_2$+5% $CO_2$ and maintained at 37° C. The contraction was recorded on a pen-and-ink recorder via an isotonic transducer.

Acetylcholine was added cumulatively to the bath to obtain a consistent dose-response curve and then test compound in various concentrations was investigated on the dose-response curve of acetylcholine before and after the treatment for 5 minutes. The contraction was expressed by a ratio to the maximal contraction with acetylcholine in the absence of test compound. The affinity of test compound to the muscarinic receptor was determined by converting into the concentration from $pA_2$ value obtained from Schild's plot. Results are shown in Table 13.

EXPERIMENTAL EXAMPLE 2

Inhibitory action on the rhythmic bladder contraction

A male rat was fixed in a supine position under the halothane anesthesia and, a catheter with rubber balloon was inserted into urinary bladder through a small incision of apex of bladder exposed by abdominal opening along the midline and the purse-string suture was performed. The catheter was led out of the upper abdominal part sutured and a three-way stopcock was connected thereto, to one of which a syringe was connected and to other of which a pressure transducer for measuring the intravesical pressure was connected. The rhythmic bladder contraction was induced by infusion of about 0.1 to 0.3 ml of water into the balloon and, after obtaining the constant amplitude of rhythmic bladder contraction, test compound was administered intraduodenally. The inhibitory effects were estimated by the reduction in amplitude of the bladder contraction.

EXPERIMENTAL EXAMPLE 3

Inhibitory action on the salivary secretion of saliva

Male rats were given with small incision in the upper abdomen under urethane anesthesia and the test compound was administered intraduodenally. Thirty minutes later, 1 mg/kg of pilocarpine was administered subcutaneously. Saliva was collected on absorbent cotton kept in the mouth at every 30 minutes from the pilocarpine administration until 1.5 hours later. Antisecretory effects were estimated by the decrease in weight of absorbent cotton.

The compounds of the present invention showed superior bladder selectivity (inhibitory activity on the salivary secretion ($ID_{30}$)/inhibitory activity on the rhythmic bladder contraction ($ED_{30}$)) to terodiline hydrochloride and oxybutynin hydrochloride being reference drugs. While the anticholinergic activity was 1/5000 to ⅓ of that of reference drugs, the inhibitory activity on bladder was 1/5 to 4 times. In particular, the inhibitory activity of compounds in Examples 1, 6 and 7 on bladder was almost equal to that of oxybutynin hydrochloride, but the inhibitory activity on the salivary secretion, one of the adverse effects, was as weak as 1/6 to 1/10.

TABLE 13

Acticholinergic activity and bladder selectivity

| Example | Anticholinergic activity ($pA_2$: $\mu M$) | Bladder selectivity Inhibitory activity on salivary secretion ($ID_{30}$) Inhibitory activity on rhythmic bladder contraction ($ED_{30}$) |
| --- | --- | --- |
| 1 | 0.79 | 5 |
| 2 | 16 | 6 |
| 3 | 3.2 | 4 |
| 4 | 2.0 | 4 |
| 6 | 2.5 | 3 |
| 7 | 1.3 | 4 |
| 14 | 5.0 | 4 |
| 41 | 6.3 | 5 |
| Terodiline hydrochloride | 0.10 | 1 |
| Oxybutynin hydrochloride | 0.0013 | 1 |

As described above, the arylglycinamide derivatives being novel compounds of the present invention exert on effect that allows the therapy of dysurias such as urinary incontinence and pollakiuria without causing dry mouth, anuresis and difficulty in micturition, which are adverse effects of conventional therapeutic drugs for urinary incontinence and pollakiuria.

What is claimed is:

1. Arylglycinamide derivatives represented by a general formula (1)

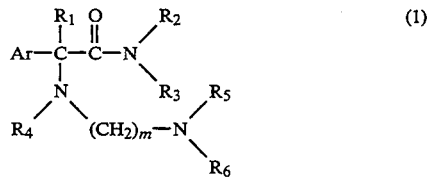

(wherein Ar denotes a phenyl group which may have 1 to 3 substituents or naphthyl group which may have 1 to 3 substituents, $R_1$ and $R_4$ denote identically or differently hydrogen atoms or lower alkyl groups with 1 to 3 carbon atoms, $R_2$ denotes a lower alkyl group with 1 to 6 carbon atoms, cycloalkyl group with 3 to 6 carbon atoms, lower alkyl group with 1 to 4 carbon atoms which may have a phenyl group which may have 1 to 3 substituents, norbornyl group, adamantyl group or phenyl group which may have 1 to 3 substituents, $R_3$ denotes a hydrogen atom or lower alkyl group with 1 to 6 carbon atoms or it may form a ring constituting alkylene together with $R_2$, $R_5$ denotes a lower alkyl group with 1 to 6 carbon atoms or cycloalkyl group with 5 or 6 carbon atoms, $R_6$ denotes a hydrogen atom or lower alkyl group with 1 to 6 carbon atoms or it may form a ring constituting alkylene together with $R_5$, and m denotes 2 or 3), and their salts.

2. A therapeutic drug for the dysurias having at least one kind of arylglycinamide represented by a general formula (1)

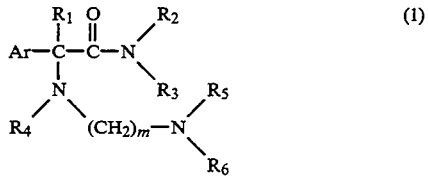

(wherein Ar denotes a phenyl group which may have 1 to 3 substituents or naphthyl group which may have 1 to 3 substituents, $R_1$ and $R_4$ denote identically or differently hydrogen atoms or lower alkyl groups with 1 to 3 carbon atoms, $R_2$ denotes a lower alkyl group with 1 to 6 carbon atoms, cycloalkyl group with 3 to 6 carbon atoms, lower alkyl group with 1 to 4 carbon atoms which may have a phenyl group which may have 1 to 3 substituents, norbornyl group, adamantyl group or phenyl group which may have 1 to 3 substituents, $R_3$ denotes a hydrogen atom or lower alkyl group with 1 to 6 carbon atoms or it may form a ring constituting alkylene together with $R_2$, $R_5$ denotes a lower alkyl group with 1 to 6 carbon atoms or cycioalkyl group with 5 or 6 carbon atoms, $R_6$ denotes a hydrogen atom or lower alkyl group with 1 to 6 carbon atoms or it may form a ring constituting alkylene together with $R_5$, and m denotes 2 or 3), and their salts as effective ingredients.

* * * * *